(12) United States Patent
Booth et al.

(10) Patent No.: US 7,736,348 B2
(45) Date of Patent: Jun. 15, 2010

(54) MEDICAL IRRIGATION BASIN AND PROCEDURAL TRAY

(75) Inventors: Charles S. Booth, Pinckney, MI (US); Donald J. Propp, Dewitt, MI (US)

(73) Assignee: Centurion Medical Products Corporation, Williamston, MI (US)

( * ) Notice: Subject to any disclaimer, the term of this patent is extended or adjusted under 35 U.S.C. 154(b) by 1081 days.

(21) Appl. No.: 11/140,459

(22) Filed: May 27, 2005

(65) Prior Publication Data

US 2006/0271017 A1 Nov. 30, 2006

(51) Int. Cl.
*A61M 1/00* (2006.01)
(52) U.S. Cl. .................. 604/317; 220/560.03
(58) Field of Classification Search .......... 604/35, 604/903, 317, 366, 385.101; 220/560.3, 220/477, 516, 613, 646, 644, 699, 570; 312/228; 119/460; 196/118; 211/119, 119.011, 88.01, 211/126.4; 4/662, 554; 5/900; 128/847; 600/563, 156, 573; 249/120, 206; 606/114; 206/565; 433/79; 33/522; 47/65.7; 99/646; 221/186
See application file for complete search history.

(56) References Cited

U.S. PATENT DOCUMENTS

| | | | |
|---|---|---|---|
| 4,160,505 A * | 7/1979 | Rauschenberger | 206/571 |
| 4,889,231 A | 12/1989 | Foote et al. | |
| 5,045,076 A | 9/1991 | Pierce | |
| 5,072,832 A * | 12/1991 | Valentine et al. | 206/570 |
| 5,441,707 A * | 8/1995 | Lewis et al. | 422/300 |
| 5,697,921 A * | 12/1997 | Blair | 604/317 |
| 5,833,055 A | 11/1998 | Cerwin et al. | |
| 6,398,062 B1 | 6/2002 | Jones | |
| 6,426,041 B1 | 7/2002 | Smith | |
| 6,585,942 B1 * | 7/2003 | Bussell et al. | 422/300 |
| 6,609,257 B1 | 8/2003 | O'Geary | |
| 6,622,864 B1 | 9/2003 | Debbs et al. | |
| 6,719,017 B1 * | 4/2004 | McArthur et al. | 141/86 |
| 6,824,853 B1 * | 11/2004 | Levine et al. | 428/77 |
| 2004/0195255 A1 * | 10/2004 | Tucker et al. | 220/793 |

* cited by examiner

*Primary Examiner*—Nicholas D Lucchesi
*Assistant Examiner*—Gerald Landry, II
(74) *Attorney, Agent, or Firm*—Fildes & Outland, P.C.

(57) ABSTRACT

A medical irrigation basin and procedural tray assembly includes a basin capable of holding irrigation fluids from irrigating a patient's wound. The basin has a bottom bounded by a perimeter. A wall extends upwards from the perimeter of the bottom and is continuous therewith. A pedestal or pedestal container fittable on the basin can support a body part and may contain useful medical fluids. A pad of absorbent material may be disposed on the bottom of the basin. The pad is adapted to absorb a substantial volume of the irrigation fluids flowing from irrigation of the patient's wound.

18 Claims, 5 Drawing Sheets

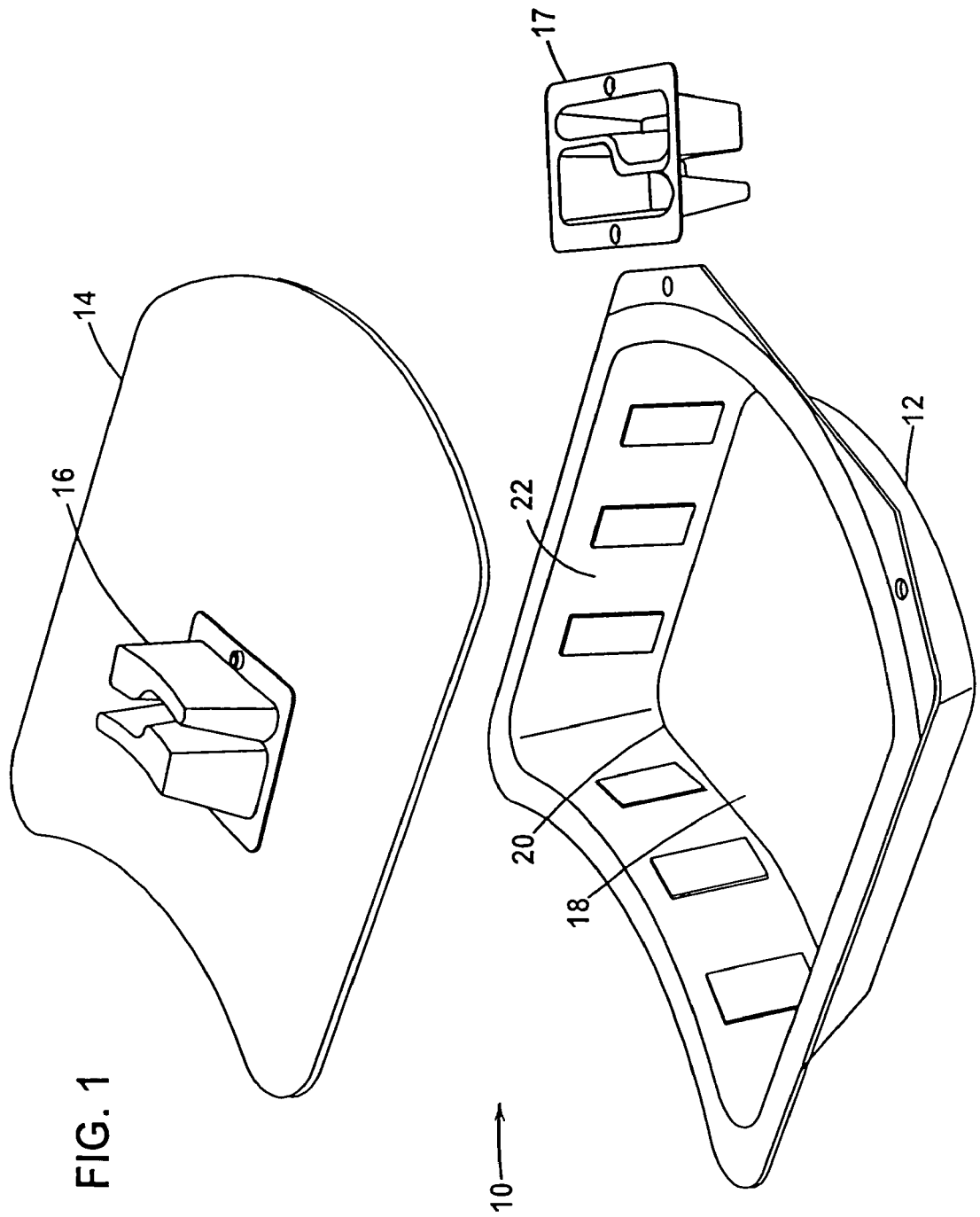

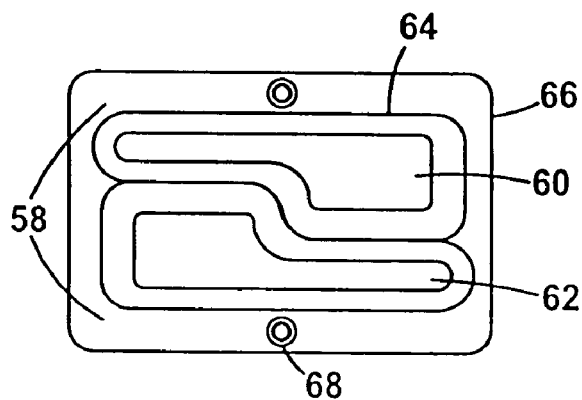
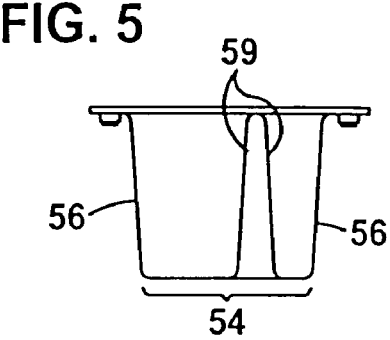
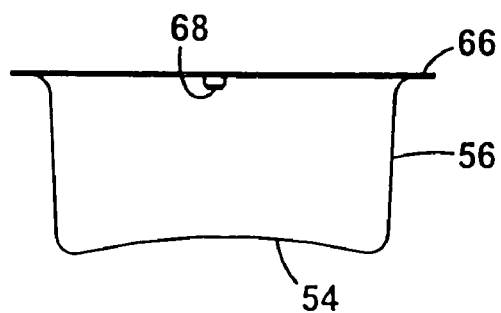
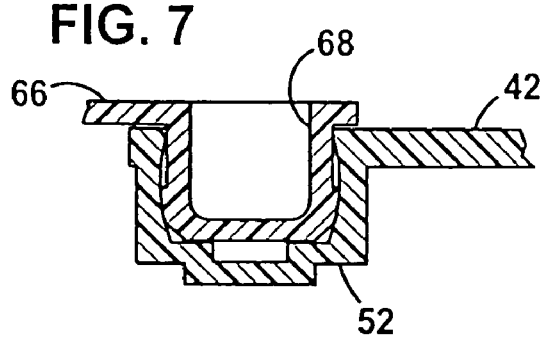

US 7,736,348 B2

MEDICAL IRRIGATION BASIN AND PROCEDURAL TRAY

TECHNICAL FIELD

This invention relates to basins used in medical procedures for collecting fluids and more specifically to basins for collecting fluids resulting from irrigating wounds or from washing body surfaces.

BACKGROUND OF THE INVENTION

It is known in the art relating to medical treatments of wounds to flush or wash the area around the wound with fluids that must be collected thereafter. Additionally, surgical procedures to treat open wounds of a patient almost always require the control and containment of blood or other bodily fluids flowing from the wound.

The resulting waste or irrigation fluids need to be contained for later transport and disposal because of possible biological or chemical contaminants that may be in the fluids. For example, the fluids may be contaminated with a number of pathogens, which could be hazardous to health care workers and others, including AIDS and Hepatitis C.

Prior art irrigation basins have several disadvantages with regards to containment, transport and disposal of collected waste fluids. One such disadvantage is that the fluids often splash onto the hard, nonabsorbent interior of a basin during the irrigation procedure, causing fluids to spray back upon the patient or health care worker. Additionally, a substantial amount of fluid, may be collected during the treatment process, making it difficult for a health care worker to move the basin without spillage.

Prior art basins too often contain rigid structures in their interior section designed to support various appendages or other features, e.g. head, neck, ankles, wrists, arms, legs, or the like, of a person's body during treatment. These structures are usually rigidly attached to the basin's interior. This can cause a problem in aligning a patient's particular feature for maximum comfort during treatment.

In addition to irrigating and cleaning a wound, medical treatment of such wound often requires the use of surgical tools that must be kept sterilized up until they are needed. Prior art techniques used to accomplish this task involve sterilizing the tools and transporting them in separate sterile sealed trays or other sterile containers. Therefore, another container, in addition to the irrigation basin, must be made available to medical professionals during a medical procedure. This can be especially problematic as specific trays and surgical peripherals must be matched up.

SUMMARY OF THE INVENTION

The present invention provides a medical irrigation basin and procedural tray assembly which provides for fluid collection and patient support and includes specific medical procedure items. The basin also includes an absorbent member or pad disposed within the basin that absorbs irrigating fluids, such as bodily fluids or waste wash fluids. By absorbing the irrigation fluids the pad helps to prevent splash back of the fluids onto a patient or health care worker.

In an exemplary embodiment of the present invention a basin assembly includes a basin capable of holding irrigation fluids from irrigating a patient's wound. The basin has a bottom bounded by a perimeter. A wall extends upwards from the perimeter of the bottom and is continuous therewith. A pedestal provided is adapted to fit on a portion of the bottom of the basin and can be positioned in the basin to support a body part. A pad of absorbent material may be disposed on the bottom of the basin. The pad is adapted to absorb a substantial volume of the irrigation fluids flowing from irrigation of the patient's wound.

In another exemplary embodiment of the present invention the basin assembly includes a dual purpose pedestal/container sized to fit on a portion of the bottom of the basin. The pedestal/container has a base shaped to fit at least one of the patient's body features, and a continuous side wall surrounding the base. When the pedestal/container is in a pedestal position, the base is raised by the side wall to support the body features during irrigation. When the pedestal/container is in an inverted container position, the base and side wall form an open container for holding liquids and or procedural items.

These and other features and advantages of the invention will be more fully understood from the following detailed description of the invention taken together with the accompanying drawings.

BRIEF DESCRIPTION OF THE DRAWINGS

In the drawings:

FIG. 1 is an exploded perspective view of a basin assembly in accordance with the present invention;

FIG. 4 is a top view of the pedestal/container of FIG. 1;

FIG. 5 is a side view the pedestal/container of FIG. 1;

FIG. 6 is another side view of the pedestal/container of FIG. 1;

FIG. 7 is an enlarged view of a retainer post and retainer pocket in accordance with the present invention taken along the line 7-7 of FIGS. 3A and 3B.

DETAILED DESCRIPTION OF THE INVENTION

Figure 2A:
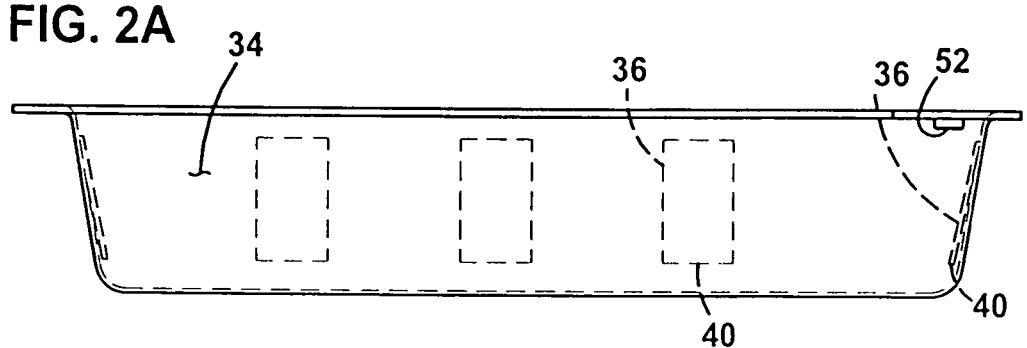
FIG. 2A is a side view of the basin of FIG. 1.

Referring to FIG. 1, numeral 10 generally indicates an exemplary embodiment of a medical irrigation basin and procedural tray assembly in accordance with the present invention. The basin assembly 10 includes an irrigation basin 12, and at least one of a removable absorbent member or pad 14, and one or more of a pedestal adapted to support a body part or dual-purpose pedestal/containers 16 and 17.

Figure 3A:
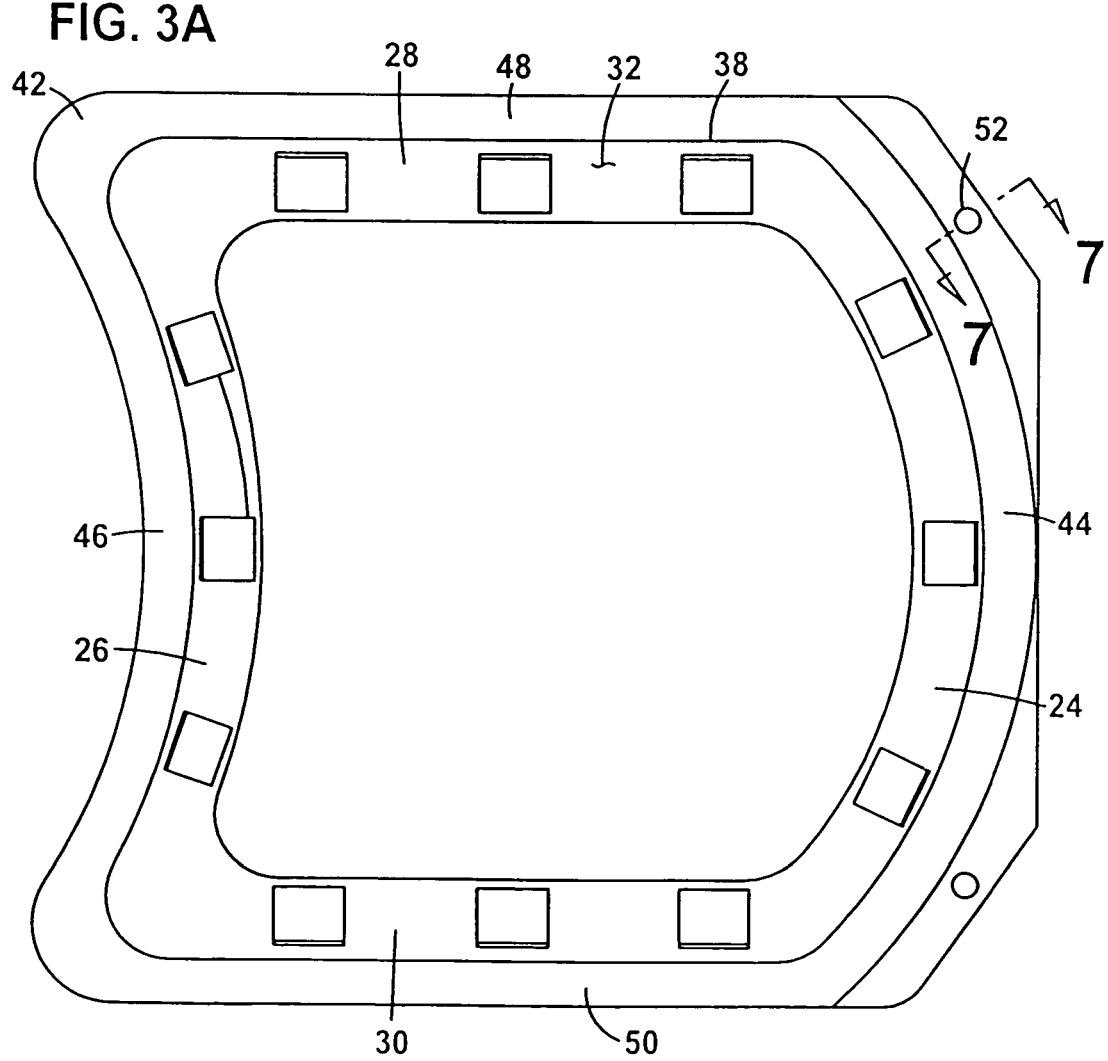
FIG. 3A is a top view of the basin of FIG. 1.

Referring to FIGS. 2A and 3A, the basin 12 is designed to retain fluids resulting from irrigating or draining a wound, or rinsing a body surface. To accomplish this the basin 12 is preferably manufactured of a molded plastic, such as high impact polystyrene (HIPS), HDPE, PETG, PVC or similar. Although various molding techniques may be used to form the basin 12 from raw material such as HIPS, a preferred technique is thermoforming.

Even though the irrigation basin 12 has been thermoformed in this embodiment to be generally square in shape, the basin can be configured into any number of shapes and sizes. For example, the basin 12 may have a rectangular, round, oval, kidney or other convenient shape.

The basin 12 has a bottom 18, which is bounded by a perimeter 20. The bottom 18 is substantially planar in shape to provide stability for the basin 12 on a flat surface. However, the bottom 18 can be of any suitable shape, for example, concave, convex, or slanted. Additionally, the bottom 18 may be shaped to accommodate various accessories such as drains or valves (not shown) to help remove excess fluids from the bottom 18 of the basin 12.

A basin wall 22 extends upwards from the perimeter 20, and runs continuously therewith. The basin wall 22 includes an outwardly curved or convex front wall section 24, and an inwardly curved or concave rear wall section 26. The front 24 and rear 26 wall sections are integrally connected by a pair of straight parallel side wall sections 28 and 30. The curvature of the rear wall section 26 is sized to comfortably fit against various features of a patient's body, such as a leg, arm, neck or the like, for irrigation of a wound.

The basin wall 22 also has an inside wall surface 32 and an outside wall surface 34. A plurality of equally spaced ribs 36 are disposed around the inside wall surface 32. The ribs 36 are angled downwardly and inwardly from a top edge 38 of the basin wall 22. The lower ends 40 of the ribs 36 are spaced an equal distance above the bottom 18 of basin 12.

A continuous rim 42 extends horizontally outward from the top edge 38 of basin wall 22, which can function as a grip or handle for the basin 12. The rim 42 includes integrally connected front 44, rear 46 and side 48, 50 rim portions extending from associated top edges of the front 24, rear 26 and side 28, 30 wall sections respectively. Disposed in the front rim portion 44 proximate the side rim portions 48 and 50 are retainer pockets 52. As will be explained in greater detail hereinafter, the retainer pockets 52 are sized to snap-fittingly receive a mating retainer post 68 (best seen in FIG. 7) of the pedestal/container 16.

Figure 2B:
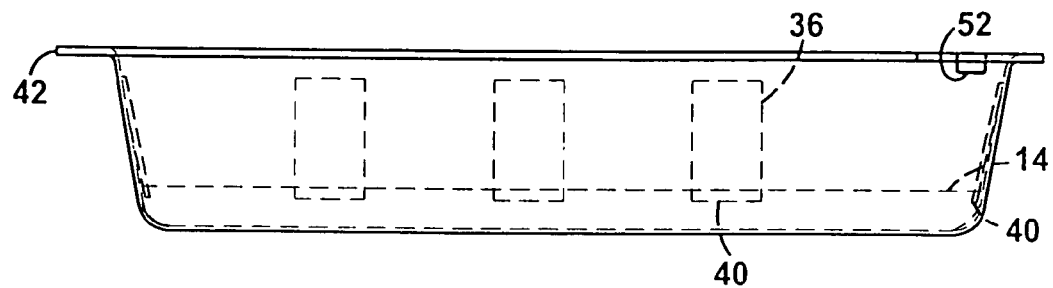
FIG. 2B is a side view of the basin of FIG. 1 with the absorbent pad disposed therein.
Figure 3B:
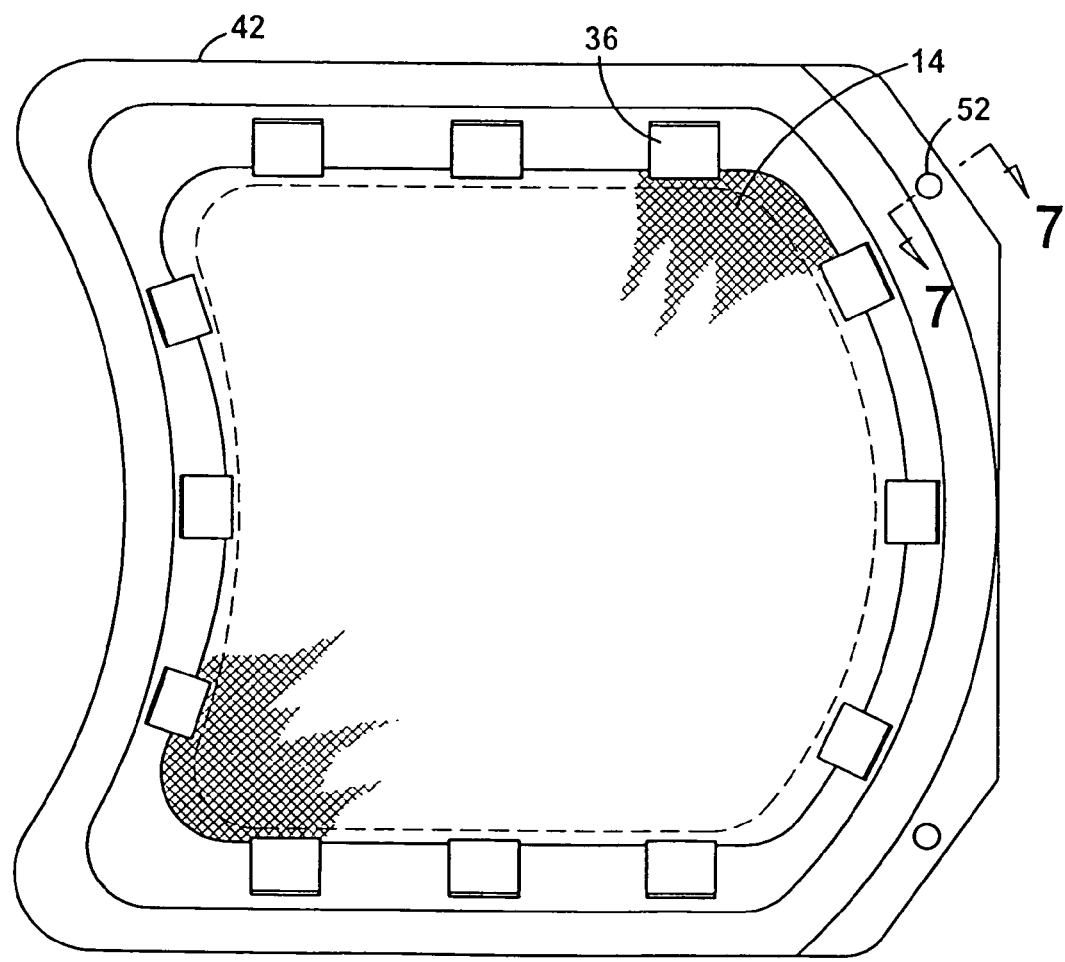
FIG. 3B is a top view of the basin of FIG. 1 with the absorbent pad disposed therein.

Referring to FIGS. 2B and 3B, the absorbent pad 14 is sized to fit in the bottom 18 of basin 12, and shaped to conform to the contour of the basin wall 22. The pad 14 is designed to absorb waste wash fluids and/or body fluids when a patient is being treated. The pad 14 may be constructed of a variety of materials including, but not limited to, any combination of an appropriate common pad material, a Super Absorbent Polymer (SAP) woven into the padding, and/or a diatomaceous earth like material.

The pad 14 is preferably die cut from a clean absorbent material, but any number of manufacturing techniques may be used to construct the pad, e.g., knife or scissors cut. Moreover, the pad 14 can be constructed of non-woven or woven laminated materials on its top and bottom surface, such as Reemay® fabric or the like, to contain a core section of material that may otherwise shed. Also the die-cut process may heat seal or crimp the edges of the laminated layers or raw absorbent material.

During operation, the pad 14 is placed in the bottom 18 of the basin 12. Any number of retaining devices may be utilized to retain the pad, 14 in the basin 12 e.g., hooks, snaps or the like. Moreover, no retaining device may be used at all, as the pad may be simply retained under it own weight.

Advantageously, when waste fluids fall into the basin 12 during treatment, the absorbent qualities of the pad 14 help to prevent the fluids from splashing back up onto a patient or health care worker. Additionally, the pad 14 is designed to absorb a substantial volume of fluid, preferably a liter or more, to alleviate the potential for spillage. Moreover, the fluids are retained within the pad for easy disposal after treatment of a patient.

Referring to FIGS. 4, 5 and 6, the pedestal or pedestal/container 16 has two functional positions. In a first or pedestal position (as illustrated by pedestal/container 16 in FIG. 1), the pedestal/container functions as a support for a patients body features, such as an arm, wrist, ankle, head or the like. Wherein the pedestal is a pedestal container, in a second or container position (as illustrated by pedestal container 17 in FIG. 1), the pedestal/container functions as a container to hold liquids, such as irrigation fluids or liquid antiseptics or alternatively to hold surgical instruments and dressings.

The pedestal/container 16 is sized to fit in the bottom 18 of the basin 12 on top of the pad 14, generally in the pedestal position. The pedestal/container 16 is preferably thermoformed of the same or similar material as the basin 12.

The pedestal/container 16 has a base 54, which is shaped to fit a variety of body features, such as a wrist, ankle, hand, foot or the like. A side wall 56 continuously surrounds the base 54 such that, when the pedestal/container 16 is in the pedestal position, the base is raised to provide support for a body feature resting upon the base 54. Alternatively, when the pedestal/container is in the container position, the side wall 56 and base 54 form a container 58 for holding liquids and/or other procedural items.

A partition 59 may be formed as an integral portion of the side wall 56 and extends from the base 54 such that the container 58 is divided into two separate compartments 60 and 62, each capable of holding a different liquid. Though the container 58 is illustrated herein as being divided into two separate compartments 60 and 62 by partition 59, one skilled in the art would recognize that any number of compartments may be formed by any number of partitions. Alternatively, the container 58 may be constructed without partitions. Additionally, it is within the scope of the present invention that the partition may not be formed as an integral portion of the side wall, but rather as an inner partition completely separated from the side wall 56.

On the edge 64 of the side wall 56 opposite the base 54, a lip 66 surrounds container 58 and projects generally horizontally outwards therefrom. On opposing sides of the lip 66 are retainer posts 68 (best seen in FIG. 7), which are sized to snap fit into retainer pocket 52. Other connecting means such as tabs and slots, hook and loop and press fit indentations or the like can be used to fasten.

Referring to FIG. 7, an enlarged view of retainer post 68 inserted into retainer pocket 52 is shown. In this configuration, the pedestal/container 16 is removeably attached to the basin 12 at their lip 66 and rim 42 respectively. As a result, the pedestal/container, in its container position, is positionally locked to the basin for added stability during the treatment process.

Though the post 68 and pocket 52 are located on the pedestal/container lip 66 and basin rim 42 respectively, it can be seen that post 68 and pocket 52 may be located on either rim 42 or lip 66. Additionally, other snap-fitting attachment structures may also be utilized, for example the pocket may be replaced with a through hole. Moreover, other attachment structures may be used other than snap-fitting attachment structures, for example, hook and loop fasteners, clips, laces or the like.

Figure 8:
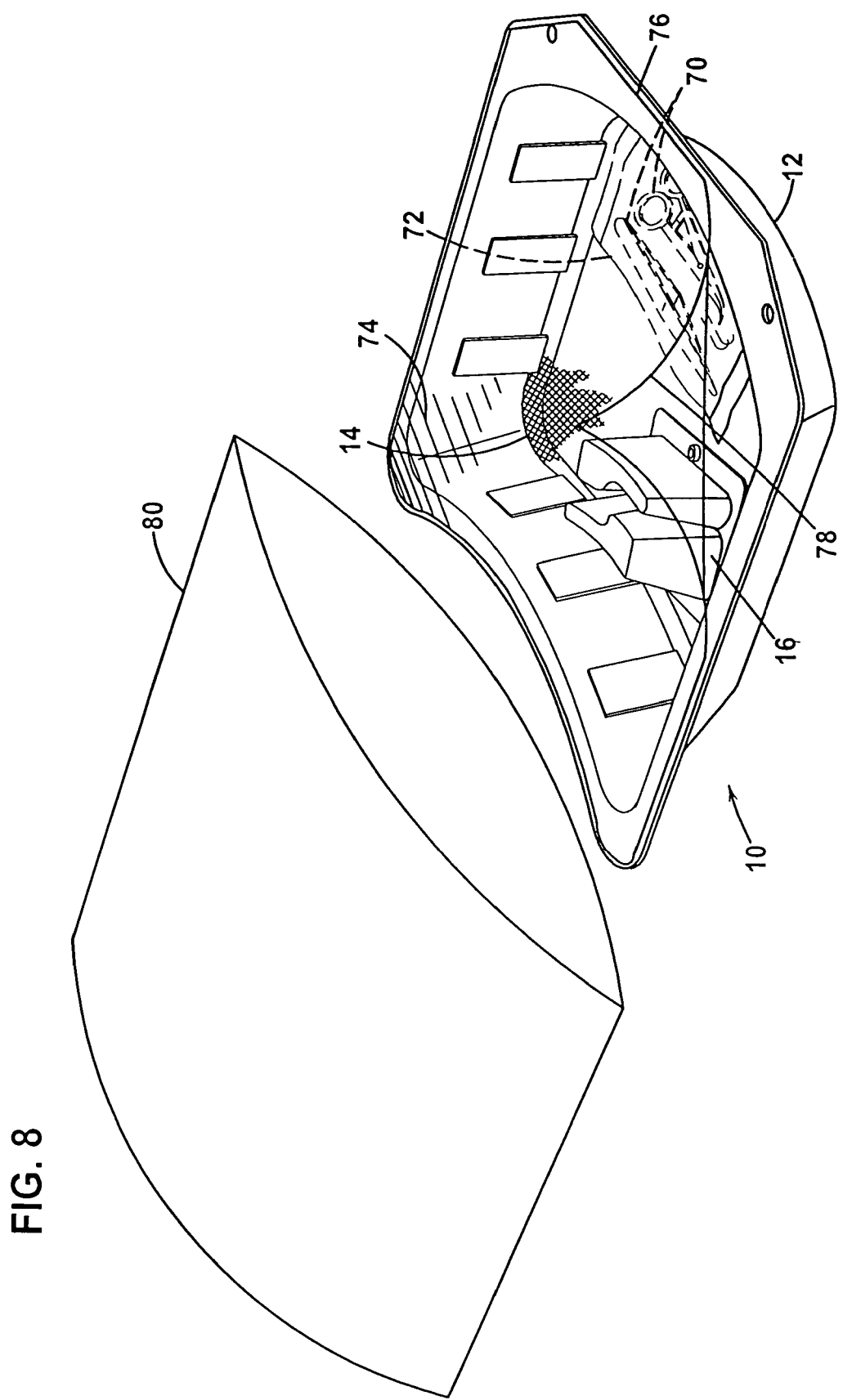
FIG. 8 is an exploded view of an exemplary embodiment of a basin assembly in its shipping configuration in accordance with the present invention.

Referring to FIG. 8, the irrigation basin assembly 10 is assembled in its shipping configuration. In this configuration the basin 12, pad 14 and pedestal/container 16 are all sterilized before shipment. Additionally, a set of custom ordered instruments 70, for purposes such as treating lacerations, are also sterilized, contained within a sterile wrap 72, and placed within the interior of the basin 12. A cover 74, preferably of plastic film, paper, TYVEK® Paper or the like is secured to the basin rim 42 via sterile seal 76. The cover 74 and sterile seal 76 maintain the sterile condition of the basin's 12 interior. After shipment to a given destination, the cover 74 may be peeled off (as illustrated by peeled section 78 of the cover 74) to break the seal 76 and expose the basin's interior.

Advantageously, by including a set of surgical instruments, such as laceration instruments in its shipping configuration, the basin assembly 10 functions as a combination irrigation basin and laceration tray. This eliminates the need to provide a separate irrigation basin, and a separate laceration tray to a medical professional during a procedure.

Optionally, a sterile external container 80, such as a plastic bag or container, may be used to contain the entire irrigation basin assembly 10 and sealed with a sterile seal as well. In this configuration, the external surfaces of the basin assembly 10 are also maintained in a sterile condition during shipping. This can be especially advantageous when the basin 12 contains external accessories, such as drains and/or valves (not shown), that must be kept sterile during shipment as well.

Although the invention has been described by reference to specific embodiments, it should be understood that numerous changes may be made within the spirit and scope of the inventive concepts described. Accordingly, it is intended that the invention not be limited to the described embodiments, but that it have the full scope defined by the language of the following claims.

What is claimed is:

1. A medical irrigation basin and procedural tray assembly for retaining irrigation fluids flowing from irrigation treatment of a patient's body, the basin assembly comprising:
   a basin capable of holding irrigation fluids from irrigating a patient's wound, said basin having,
      a continuous, impermeable bottom bounded by a perimeter, and
      a wall extending upwards from said perimeter of said bottom and continuous therewith; and
   a pedestal separate and independent of said basin;
   said pedestal adapted to be moveable relative to and positionable within said basin, said pedestal having:
      a base having a shape adapted to fit at least one of said patient's body features;
      a side wall generally surrounding said base; and
      at least one partition extending from said base such that said pedestal is divided into at least two separate compartments, each capable of holding a separate liquid;
   wherein, when said pedestal is in a pedestal position said base is raised by said side wall to support said body features during irrigation.

2. The basin of claim 1 including a pad of absorbent material disposed on said bottom of said basin, said pad adapted to absorb a substantial volume of said irrigation fluids flowing from irrigation of said patient's wound.

3. The basin assembly of claim 2 wherein the basin comprises a plurality of retaining devices disposed on said basin wall to retain said pad within said basin.

4. The basin assembly of claim 1 wherein at least a portion of said wall is anatomically contoured to fit against at least one of said patient's body features for irrigation of said wound.

5. The basin assembly of claim 2 wherein said pad is removeable from said basin.

6. The basin assembly of claim 2 wherein said pad is capable of holding at least one liter of said irrigation fluid.

7. The basin assembly of claim 1 wherein said pedestal is a dual purpose pedestal/container sized to fit on a portion of said bottom of said basin, said pedestal/container having:
   a base shaped to fit at least one of said patient's body features; and
   a continuous side wall surrounding said base;
   wherein, when said pedestal/container is in a pedestal position said base is raised by said side wall to support said body features during irrigation, and, when said pedestal/container is in an inverted container position said base and side wall form an open container for holding liquids.

8. The basin assembly of claim 7 comprising:
   said basin having a rim extending generally horizontally outward from a top edge of said basin wall, and further having a basin attachment structure disposed in said rim; and
   said pedestal/container having a lip extending generally horizontally outward from an edge of said pedestal/container side wall, and further having a pedestal/container attachment structure disposed in said lip;
   wherein said basin attachment structure and said pedestal/container attachment structure are adapted to removeably attach to each other when said pedestal/container is in said container position.

9. The basin assembly of claim 8 comprising:
   said basin attachment structure being one of a retainer post and a retainer pocket; and
   said pedestal/container attachment structure being the other of said retainer post and retainer pocket;
   wherein said retainer post snap fits into said retainer pocket to removeably attach said basin to said pedestal/container.

10. The basin assembly of claim 1 comprising:
    said basin having a rim extending generally horizontally outward from a top edge of said basin wall; and
    a cover secured to said rim via a sterile seal to form an inner sealed portion of said basin;
    wherein said inner sealed portion of said basin is maintained in a sterile condition.

11. The basin assembly of claim 10 comprising:
    a set of surgical instruments for a medical procedure contained within the inner sealed portion of said basin.

12. The basin assembly of claim 11 wherein the instruments are contained within a sterile wrap.

13. The basin assembly of claim 10 comprising:
    said basin having a sterile external surface;
    a sterile external container containing and sealing said basin assembly within its interior via sterile seal to maintain said basin external surfaces in said sterile condition.

14. A medical irrigation basin and procedural tray assembly for retaining irrigation fluids flowing from irrigation treatment of a patient's body, the basin assembly comprising:
    a basin capable of holding irrigation fluids from irrigating a patient's wound, said basin having,
       a continuous, impermeable bottom bounded by a perimeter, and
       a wall extending upwards from said perimeter of said bottom and continuous therewith; and
    a dual purpose pedestal/container separate and independent of said basin;
    said pedestal/container adapted to be moveable relative to and positionable within said basin, said pedestal/container having:
       a base shaped to fit at least one of said patient's body features;
       a continuous side wall surrounding said base; and
       at least one partition extending from said base such that said container is divided into at least two separate compartments, each capable of holding a separate liquid when said pedestal/container is in an inverted container position;

wherein, when said pedestal/container is in a pedestal position said base is raised by said side wall to support said body features during irrigation.

15. The basin assembly of claim 14 comprising:
said basin having a rim extending generally horizontally outward from a top edge of said basin wall, and further having a basin attachment structure disposed in said rim; and
said pedestal/container having a lip extending generally horizontally outward from an edge of said pedestal/container side wall, and further having a pedestal/container attachment structure disposed in said lip;
wherein said basin attachment structure and said pedestal/container attachment structure are adapted to removeably attach to each other when said pedestal/container is in said container position.

16. The basin assembly of claim 15 comprising:
said basin attachment structure being one of a retainer post and a retainer pocket; and
said pedestal/container attachment structure being the other of said retainer post and retainer pocket;
wherein said retainer post snap fits into said retainer pocket to removeably attach said basin to said pedestal/container.

17. The basin assembly of claim 7 including a pad of absorbent material disposed on said bottom of said basin, said pad adapted to absorb a substantial volume of said irrigation fluids flowing from irrigation of said patient's wound.

18. A medical irrigation basin and procedural tray assembly for retaining irrigation fluids flowing from irrigation treatment of a patient's body, the basin assembly comprising:
a basin capable of holding irrigation fluids from irrigating a patient's wound, said basin having:
a continuous, impermeable bottom bounded by a perimeter,
a wall extending upwards from said perimeter of said bottom and continuous therewith,
a rim extending generally horizontally outward from a top edge of said basin wall, and
a basin attachment structure disposed in said rim, said basin attachment structure being one of a retainer post and a retainer pocket; and
a pedestal separate and independent of said basin;
said pedestal adapted to be moveable relative to and positionable within said basin, said pedestal having:
a base having a shape adapted to fit at least one of said patient's body features,
a side wall generally surrounding said base,
a lip extending generally horizontally outward from an edge of said pedestal side wall, and
a pedestal attachment structure disposed in said lip, said pedestal attachment structure being the other of said retainer post and retainer pocket;
said retainer post snap fits into said retainer pocket to removeably attach said basin to said pedestal;
said pedestal base is raised by said pedestal side wall in a pedestal position to support said body features during irrigation, and said basin attachment structure and said pedestal attachment structure are removeably attached to each other when said pedestal is in an inverted container position.

* * * * *